United States Patent [19]

Goettsch et al.

[11] 4,216,151

[45] Aug. 5, 1980

[54] PROCESS FOR THE RECOVERY OF 2-PYRROLIDONE

[75] Inventors: Reijer Goettsch, Beek; Arnold G. M. Jetten, Moorveld, both of Netherlands

[73] Assignee: Stamicarbon, B.V., Geleen, Netherlands

[21] Appl. No.: 964,790

[22] Filed: Nov. 28, 1978

[30] Foreign Application Priority Data

Dec. 2, 1977 [NL] Netherlands .......................... 7713349

[51] Int. Cl.² ............................................. C07D 207/26
[52] U.S. Cl. ........................................... 260/326.5 FN
[58] Field of Search ............................. 260/326.5 FN

[56] References Cited

U.S. PATENT DOCUMENTS

| 3,966,763 | 6/1976 | Greene | 3260/26.5 FN |
| 4,014,900 | 3/1977 | Pusztaszeri | 260/326.5 FN |
| 4,036,836 | 7/1977 | Greene | 260/326.5 FN |
| 4,042,599 | 8/1977 | Greene | 260/326.5 FN |
| 4,050,994 | 9/1977 | Anshus | 260/326.5 FN |
| 4,123,438 | 10/1978 | Geurts et al. | 260/326.5 FN |

*Primary Examiner*—Jose Tovar
*Attorney, Agent, or Firm*—Cushman, Darby & Cushman

[57] ABSTRACT

A process for the recovery of 2-pyrrolidone from the aqueous reaction product obtained in the preparation of 2-pyrrolidone from the hydrogenation of succinonitrile and subsequent reaction with water of the hydrogenation product thus obtained. The aqueous reaction mixture is adjusted to a pH value of 7 or lower and extracted with chloroform or methylene chloride to form an organic phase containing substantially all of the 2-pyrrolidone. The 2-pyrrolidone can be recovered from the organic phase by distillation, or by further extraction with water followed by crystallization from the aqueous phase thus formed or by evaporation of water.

12 Claims, No Drawings

PROCESS FOR THE RECOVERY OF 2-PYRROLIDONE

BACKGROUND OF THE INVENTION

The present invention relates to a process for the recovery of 2-pyrrolidone from the reaction product obtained in the preparation of 2-pyrrolidone.

A suitable method for preparing 2-pyrrolidone is the hydrogenation of succinonitrile and reaction with water of the hydrogenation product thus formed, resulting in an aqueous reaction product containing 2-pyrrolidone and impurities. Two processes of this type are disclosed in U.S. Pat. No. 3,644,402, and in U.S. Pat. application Ser. No. 829,781, filed Sept. 1, 1977. These methods yield an aqueous reaction product from which 2-pyrrolidone of quite high purity can be recovered by fractional distillation. However, it has been found that a considerable amount of 2-pyrrolidone, for example up to about 7% of the total present in the reaction product, is lost during the course of this distillation and cannot be recovered.

It is therefore an objective of this invention to provide a method for the recovery of substantially pure 2-pyrrolidone from an aqueous reaction product containing 2-pyrrolidone and impurities whereby the loss of 2-pyrrolidone can be substantially reduced relative to the known distillation recovery method.

DETAILED DESCRIPTION OF THE INVENTION

The process of the invention for the recovery of 2-pyrrolidone from an aqueous solution of the reaction mixture obtained by the hydrogenation of succinonitrile and the subsequent reaction with water of the hydrogenation product thus formed essentially comprises adjusting the pH of the aqueous solution of reaction mixture to a value of at most 7, and subjecting it to an extraction with chloroform or methylene chloride. This results in the formation of an organic phase containing 2-pyrrolidone and at most a minor portion of the impurities, and a residual aqueous phase containing impurities, and at most a minor portion of the 2-pyrrolidone. Preferably such residual aqueous phase will be substantially free of 2-pyrrolidone. The 2-pyrrolidone is thereafter recovered from this organic phase.

This extraction with chloroform or methylene chloride may be carried out directly on the aqueous reaction mixture containing 2-pyrrolidone as it is obtained in the preparation of 2-pyrrolidone from succinonitrile. However, the 2-pyrrolidone concentration of such an aqueous reaction mixture is normally comparatively low, and preferably is raised to a concentration of, for example 50% to 60% by weight, by removing part of the water by distillation, before being extracted. The removal of part of the water by distillation has the additional advantage that the more volatile impurities are also thereby removed from the solution.

The pH of the aqueous solution of reaction mixture can be adjusted to the desired value by adding acid, such as sulphuric acid or acetic acid, or by forming an acid in situ in the solution, such as by passing carbon dioxide through the aqueous solution. However, other acids or other methods of forming acids in situ may also be utilized. Various pH values of 7 or below may be used, but a pH lower than 1, although it may be used in principle, offers no advantage. Preferably, use is made of a pH of between of about 2 and 6, because such a pH has been found to have a favorable effect on the purity of the 2-pyrrolidone recovered.

The extraction of the aqueous solution of reaction mixture can effectively be carried out in counter-current to the organic phase at a temperature of, for example, between about 15 and 90° C. Preferably, however, this extraction is carried out at temperatures of between about 15° and 45° C. so that atmospheric pressure may be used.

The amount of organic solvent to be used as extraction agent should generally be in the range of between about 2 and 20 times, by weight, the amount of 2-pyrrolidone present in the aqueous solution of reaction mixture to be extracted. If chloroform is used as the extraction agent, a very favorable separation is effected between the impurities in the aqueous phase, and the 2-pyrrolidone which is extracted into the organic phase. Preferably the aqueous phase after extraction will be substantially free of 2-pyrrolidone. If so desired, the organic phase so obtained may be washed with some water.

The impurities initially present in the aqueous solution include by-products formed in the preparation of 2-pyrrolidone, such as 1,4-diaminobutane which can be recovered from the aqueous phase remaining after the extraction with organic solvents.

The recovery of the 2-pyrrolidone from the organic phase formed in the extraction of the aqueous solution of the reaction mixture can be accomplished in various ways. For example, the organic solvent may be removed by evaporation, or the 2-pyrrolidone may be made to crystallize. Preferably, it has been found that a very complete recovery of a substantially pure 2-pyrrolidone product can be achieved by a second extraction wherein the organic phase from the first extraction is extracted with water, resulting in a second aqueous phase containing 2-pyrrolidone and only a minor portion of the impurities contained in the first organic phase, and a second organic phase containing only a minor portion of 2-pyrrolidone. Preferably this second organic phase will be substantially free of 2-pyrrolidone. The 2-pyrrolidone can be recovered from the second aqueous phase by crystallization from the solution, or by evaporation of water.

The amount of water to be used as extraction agent in this second extraction should generally be in the range of between about 1 and 8 times, by weight, the amount of 2-pyrrolidone present in the organic phase from the first extraction. Preferably, this second extraction is carried out at a temperature of between about 15 and 50° C. If desired, the 2-pyrrolidone recovered from the aqueous phase of this second extraction can be subjected to distillation to still further increase its purity. Very little 2-pyrrolidone is lost in this final distillation, particularly when compared to the loss of 2-pyrrolidone generaly experienced in the known recovery processes wherein the aqueous reaction mixture is itself directly distilled to obtain the 2-pyrrolidone product.

The invention will be further elucidated in the following Examples. In Examples I and II the recovery is carried out in accordance with the invention, and the significantly higher loss of 2-pyrrolidone resulting from the known distillation recovery process is shown in the Comparative Example.

EXAMPLE I

A relatively dilute aqueous reaction mixture of 2-pyrrolidone is obtained by hydrogenation of succinonitrile and reaction with water of the resulting hydrogenated product in the manner described in the above-mentioned U.S. Pat. application Ser. No. 829,781. This aqueous reaction mixture is concentrated by evaporation of water to form an aqueous solution of the reaction mixture containing 51% by weight of 2-pyrrolidone, 40% by weight of water, and 9% by weight of other compounds, including 1,4-diaminobutane. The pH of this aqueous solution is lowered from its original value of 12 to a value of 5 by adding sulphuric acid (96% by weight) to the concentrated solution. The resulting pH adjusted aqueous solution is extracted at 25° C. in a column in counter-current flow with chloroform in an amount of 289 grams of chloroform for every 100 grams of aqueous solution. The resulting organic phase contains 15% by weight of 2-pyrrolidone, while hardly any 2-pyrrolidone is contained in the aqeous phase, and the extraction efficiency amount to 99.9%. The resulting first organic phase is then extracted in counter-current flow with water at a temperature of 25° C. in an amount of 35 grams of water for every 100 grams of such first organic phase. The efficiency of this extraction is also 99.9%. The chloroform still contained in the resulting second aqueous phase is removed by evaporation, after which an aqueous solution remains that contains 28.9% by weight of 2-pyrrolidone having a purity of 99%. The 1,4-diaminobutane originally present in the reaction mixture can no longer be detected in this aqueous solution. After distillation of this 2-pyrrolidone at 133° C., 12 mm of Hg, its purity is 99.6%. Only 1.7% is the 2-pyrrolidone contained in the product to be distilled gets lost in the distillation, and the total loss of 2-pyrrolidone is only about 2% relative to the original amount of 2-pyrrolidone present in the initial aqueous reaction mixture.

COMPARATIVE EXAMPLE

An aqueous reaction mixture similar to that used as the starting point in Example I is subjected to fractional distillation. At 133° C. and 12 mm of Hg, a fraction containing 2-pyrrolidone is obtained which has a purity of 99% by weight. The loss of 2-pyrrolidone amounts to 7% of the original amount of 2-pyrrolidone present in the initial aqueous reaction mixture.

EXAMPLE II

A relatively dilute aqueous reaction mixture of 2-pyrrolidone is obtained by hydrogenation of succinonitrile and reaction with water of the resulting hydrogenated product in the manner described in the above-mentioned U.S. Pat. application Ser. No. 829,781. This aqueous reaction mixture is concentrated by evaporation of water to form an aqueous solution of the reaction mixture containing 60% by weight of 2-pyrrolidone, 30% by weight of water and 10% by weight of other compounds. The pH of this aqueous solution is lowered from its original value of 12 to a value of 5 by adding 96% by weight sulphuric acid. Next, the resulting pH adjusted aqueous solution is extracted at 25° C. in counter-current flow with 540 grams of methylene chloride for every 100 grams of solution, and the extraction efficiency amounts to 99.9%. The resulting first organic phase, containing about 10% by weight 2-pyrrolidone, is then extracted at 25° C. in counter-current flow with 35 grams of water for every 100 grams of first organic phase, resulting in an extraction efficiency of 99.9%. Solid 2-pyrrolidone, having a purity of 99%, is recovered by evaporation of the water from the resulting second aqueous solution. The purity of this solid 2-pyrrolidone is further increased to 99.5% by distillation at 133° C. at a reduced pressure of 12 mm of Hg. The loss of 2-pyrrolidone in this distillation is only 1.4% relative to the amount of 2-pyrrolidone present in the product to be distilled, and the total loss of pyrrolidone is only about 1.8% relative to the original amount of 2-pyrrolidone present in the initial aqueous reaction mixture.

What is claimed is:

1. A process for the recovery of 2-pyrrolidone from an aqueous solution of the reaction product formed by the hydrogenation of succinonitrile and subsequent reaction of the hydrogenation product thus obtained with water, said aqueous solution containing 2-pyrrolidone and impurities, said process essentially comprising the steps of:

adjusting said aqueous solution of a pH value of at most 7;

extracting said pH adjusted aqueous solution with an organic solvent selected from the group consisting of chloroform and methylene chloride, thereby forming a first organic phase of said solvent consisting 2-pyrrolidone and at most a minor portion of said impurities, and a first aqueous phase containing said impurities and at most a minor portion of said 2-pyrrolidone;

recovering 2-pyrrolidone from said first organic phase.

2. The process of claim 1 wherein said aqueous solution containing 2-pyrrolidone and impurities is first concentrated with respect to 2-pyrrolidone by evaporation of water prior to extraction.

3. The process of claim 1 wherein said organic solvent is chloroform.

4. The process of claim 1 wherein said aqueous solution is adjusted to pH value of from about 2 to 6.

5. The process of claim 1 wherein the 2-pyrrolidone recovered from said first organic phase is thereafter subjected to a distillation to further increase its purity.

6. The process of claim 1 wherein the amount of organic solvent utilized in said extraction is within the range of from about 2 to 20 times by weight the amount of 2-pyrrolidone present in said aqueous solution.

7. The process of claim 1 wherein said first aqueous phase is substantially free of 2-pyrrolidone.

8. The process of claim 1 wherein 2-pyrrolidone is recovered from said first organic phase by the additional steps of:

extracting said first organic phase with water thereby forming a second aqueous phase containing 2-pyrrolidone and at most a minor portion of the impurities contained in said first organic phase, and a second organic phase containing impurities and at most a minor portion of said 2-pyrrolidone; and recovering 2-pyrrolidone from said second aqueous phase.

9. The process of claim 8 wherein said 2-pyrrolidone is recovered from said second aqueous phase by evaporation of water.

10. The process of claim 8 wherein said 2-pyrrolidone is recovered by crystallization from said second aqueous phase.

11. The process of claim 8 wherein said 2-pyrrolidone recovered from said second aqueous phase is thereafter subjected to a distillation to further increase its purity.

12. The process of claim 8 wherein said second organic phase is substantially free of 2-pyrrolidone.

* * * * *